United States Patent
Proksa

(10) Patent No.: US 9,775,575 B2
(45) Date of Patent: Oct. 3, 2017

(54) DARK-FIELD IMAGING

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 226 days.

(21) Appl. No.: 14/405,418

(22) PCT Filed: Jun. 26, 2013

(86) PCT No.: PCT/IB2013/055244
§ 371 (c)(1),
(2) Date: Dec. 4, 2014

(87) PCT Pub. No.: WO2014/002026
PCT Pub. Date: Jan. 3, 2014

(65) Prior Publication Data
US 2015/0139383 A1    May 21, 2015

Related U.S. Application Data

(60) Provisional application No. 61/664,943, filed on Jun. 27, 2012.

(51) Int. Cl.
*A61B 6/00* (2006.01)
*G01N 23/04* (2006.01)
(Continued)

(52) U.S. Cl.
CPC .............. *A61B 6/484* (2013.01); *A61B 6/032* (2013.01); *A61B 6/4035* (2013.01);
(Continued)

(58) Field of Classification Search
CPC ...................................... A61B 6/484
See application file for complete search history.

(56) References Cited

U.S. PATENT DOCUMENTS

2005/0228271 A1   10/2005   Diebold et al.
2010/0074395 A1*   3/2010   Popescu ................... A61B 6/06
378/16
(Continued)

FOREIGN PATENT DOCUMENTS

WO    2012000694 A1    1/2012
WO    2013171657 A1   11/2013

OTHER PUBLICATIONS

Cong, W., et al.; Dark-field Tomography: Modeling and Reconstruction; 2010; http://arxiv.org/abs/1003.2155v1.
(Continued)

*Primary Examiner* — Dani Fox

(57) ABSTRACT

A method for dark-field imaging includes acquiring dark-field image projections of an object with an imaging apparatus that includes an x-ray interferometer, applying a pressure wave having a predetermined frequency to the object for each acquired projection, wherein the predetermined frequency is different for each projection, and processing the acquired projections, thereby generating a 3D image of the object. In other words, the method corresponds to acoustically modulated X-ray dark field tomography. An imaging system (400) includes a scanner (401) configured for dark-field imaging, the scanner including: a source/detector pair (402/408) and a subject support (416), a pressure wave generator (420) configured to generate and transmit pressure waves having predetermined frequencies, and a console (424) that controls the scanner and the pressure wave generator to acquire at least two dark-field projection of an object with different pressure waves having different frequencies applied to the object.

22 Claims, 4 Drawing Sheets

Figure 1:
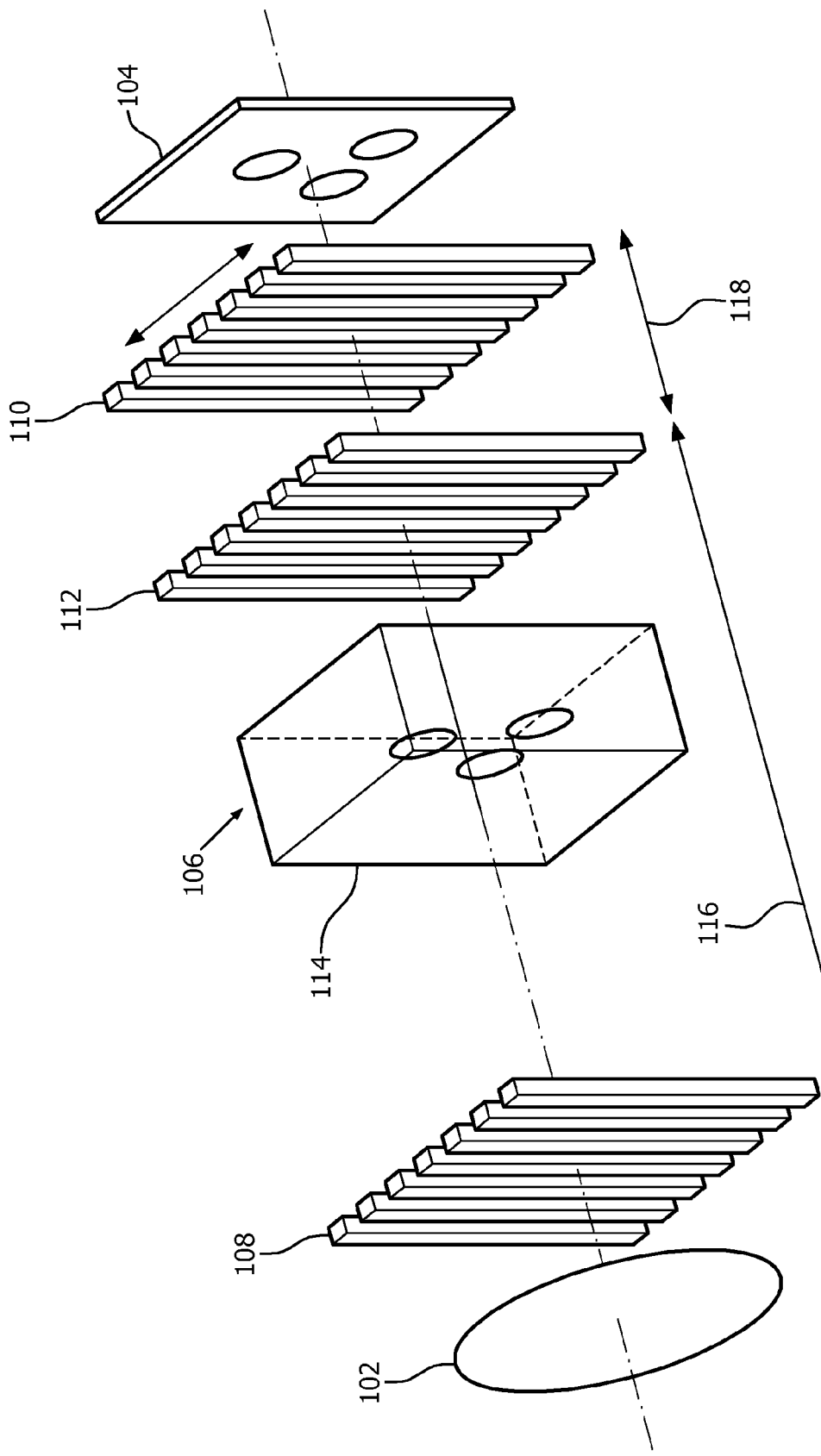

(51) Int. Cl.
*G06T 11/00* (2006.01)
*G06T 1/00* (2006.01)
*A61B 6/03* (2006.01)

(52) U.S. Cl.
CPC ............ *A61B 6/4291* (2013.01); *A61B 6/486* (2013.01); *A61B 6/5205* (2013.01); *G01N 23/046* (2013.01); *G06T 1/0007* (2013.01); *G06T 11/006* (2013.01); *G01N 2223/419* (2013.01); *G01N 2223/612* (2013.01); *G06T 2200/04* (2013.01); *G06T 2210/41* (2013.01); *G06T 2211/424* (2013.01)

(56) References Cited

U.S. PATENT DOCUMENTS

2011/0142316 A1    6/2011    Wang et al.
2012/0243658 A1    9/2012    Geller et al.

OTHER PUBLICATIONS

Hamilton, T. J., et al.; Acoustically modulated x-ray phase contrast imaging; 2004; Physics in Medicine and Biology; 49(21)4985.
Hamilton, T. J., et al.; X-ray elastography: Modification of x-ray phase contrast images using ultrasonic radiation pressure; 2009; J. Appl. Phys.; 105; 4 pages.
Hamilton, T. J., et al.; Ultrasonically Modulated X-Ray Phase Contrast and Vibration Potential Imaging Methods; 2006; Proc. of SPIE; vol. 6086:1-11.
Liu, Y., et al.; Tomography-Based 3-D Anisotropic Elastography Using Boundary Measurements; 2005; IEEE Trans. on Medical Imaging; 24(10)1323-1333.
Wang, L. V., et al.; Frequency-swept ultrasound-modulated optical tomography of scattering media; 1998; Optics Letters; 23(12)975-977.
Zhou, et el., "Development of Phase-Contrast X-Ray Imaging Techniques and Potential Medical Applications", Physica Medica (2008) 24, 129-147.

\* cited by examiner

DARK-FIELD IMAGING

CROSS REFERENCE TO RELATED APPLICATIONS

This application is a national filing PCT application Serial No. PCT/IB2013/055244, filed Jun. 26, 2013, published as WO 2014/002026 A1 on Jan. 3, 2014, which claims the benefit of U.S. provisional application Ser. No. 61/664,943 filed Jun. 27, 2012, which is incorporated herein by reference.

The following generally relates to dark-field dark field imaging and is described with particular application to computed tomography (CT).

In conventional CT imaging, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, in cases where different forms of tissue with similar absorption cross-sections are under investigation (e.g., mammography or angiography), the X-ray absorption contrast is relatively poor. Consequently, differentiating pathologic from non-pathologic tissue in an absorption radiograph obtained with a current hospital-based X-ray system remains difficult for certain tissue compositions.

Dark-field (or grating-based differential phase-contrast) imaging overcomes the above-noted contrast limitation. Generally, such imaging utilizes X-ray gratings, which allow the acquisition of X-ray images in phase contrast, which provides additional information about the scanned object. With dark-field imaging, an image is generated that is based on the scatter components of the X-ray radiation diffracted by the scanned object. Very slight density differences in the scanned object then can be shown at very high resolution. An example imaging system configured for dark-filed imaging is discussed in application Ser. No. 13/514,682, filed Jun. 8, 2012, entitled "Phase Contrast Imaging," and assigned to Koninklijke Philips Electronics N.V., the entirety of which is incorporated herein by reference.

The apparatus described in Ser. No. 13/514,682 is shown in FIG. 1 and includes an X-ray source 102 and a detector array 104 located opposite each other across an examination region 106. A source grating 108 is adjacent to the source 102, an absorber (or analyzer) grating 110 is adjacent to the detector array 104, and a phase grating 112 is between an object 114 and the absorber grating 110. The source grating 108 is separated from the phase grating 112 by a distance ("l") 116. The phase grating 112 is separated from the absorber grating 110 by a distance ("d") 118, which corresponds to the Talbot distance ($d=p_1^2/8\lambda$, where $\lambda$ is the wavelength of the incident radiation).

The source grating 108, the phase grating 112, and the absorber grating 110 respectively have grating line periods $p_0$, $p_1$ and $p_2$, where $$p_2 = \frac{1}{d}p_0 \text{ and } p_2 = \frac{1}{2}p_1 \cdot \frac{(d+1)}{1}.$$

The source grating 108 creates an array of individually coherent, but mutually incoherent sources. The object 114 in the beam path causes a slight refraction for each coherent subset of X-rays, which is proportional to the local phase gradient of the object. This small angular deviation results in changes of the locally transmitted intensity through the combination of the phase gratings 112 and the absorber grating 110.

The phase grating 112 acts as a beam splitter and divides an incoming X-ray beam essentially into the two first diffraction orders. The diffracted beams interfere and form, in Talbot distances, linear periodic fringe patterns with a periodicity that equals half the phase grating times the geometric magnification factor defined by 1/(l+d). Perturbations of the incident wave front, such as those induced by refraction on the object 114 in the beam, lead to local displacement of the fringes. The absorber grating 110 acts as a transmission mask for the detector array 104 and transforms local fringe positions into signal intensity variations. The detected signal profile hence contains quantitative information about the phase shift induced by the object 114.

To code and extract the phase information, a phase-stepping approach has been utilized. With this approach, the absorber grating 110, relative to the phase grating 112, is translated in a transverse direction, which is perpendicular to the lines of gratings, via predetermined step size movements over a grating lines period. At each grating step, a measurement is taken, and several (e.g., eight) grating steps and measurements are taken for a projection. For 3D acquisitions, the object 114 is rotated relative to the source 102, the gratings 108, 110 and 112, and the detector array 104, or the source 102, the gratings 108, 110 and 112, and the detector array 104 are rotated around the object 114 (over at least 180 degrees plus a fan angle), with a predetermined number of projections (e.g., 1000) acquired from different angular views of the rotation.

Figure 3:
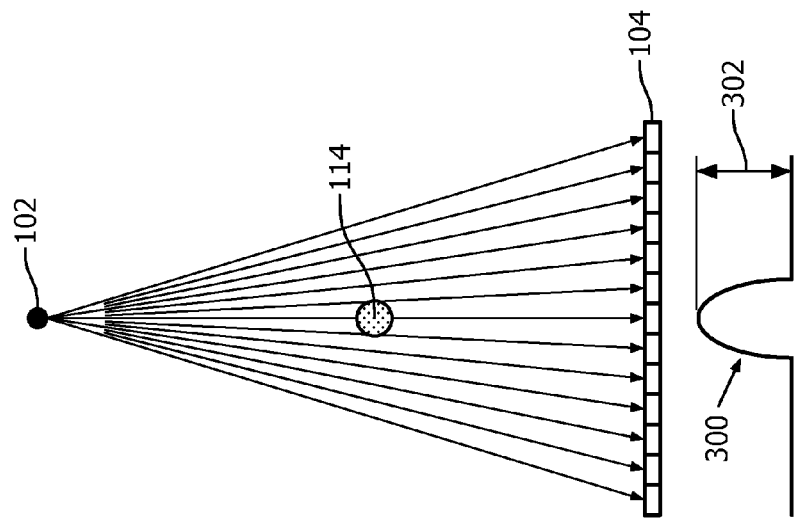
Figure 2:
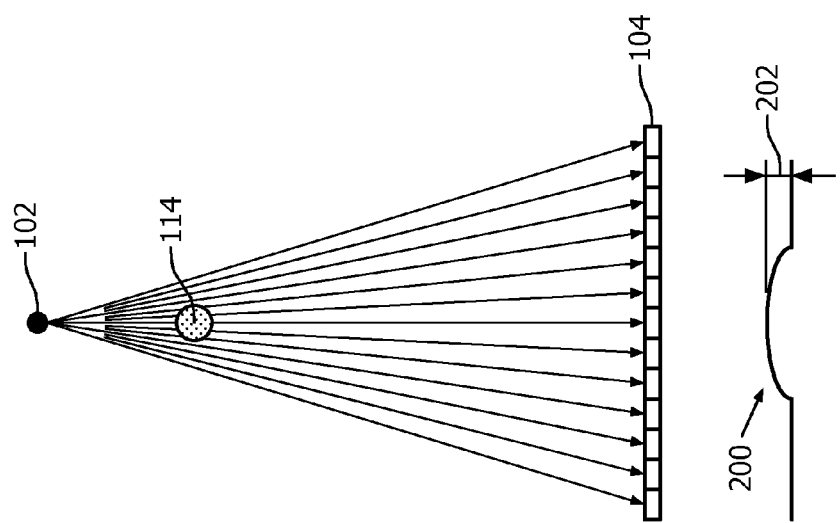

Each pixel in the dark field image represents a line integral of the second moment of the small angle scattering distribution. However, the contribution to the line integral depends on the relative position of the object 114 in the examination region 106 between the source 102 and detector array 104, due to inverse signal magnification. This is shown in FIGS. 2 and 3. In FIG. 2, the object 114 is closer to the source 102 relative to the position of the object 114 in FIG. 3. As a result, a maximum height 202 of a detector array profile 200 for the object location in FIG. 2 will be smaller relative to a maximum height 302 of a detector array profile 300 for the object location in FIG. 3. Generally, inverse signal magnification scales the height of the detected signal inversely with respect to the position of the object 114 between the source 102 and the detector array 104.

The attenuation of an X-ray along a path from the source 102 through the object 114 and to the detector array 104 occurs as shown in EQUATION 1:

$$I = I_0 e^{-\int_0^1 f(\vec{s}+l\vec{r})dl} \qquad \text{EQUATION 1}$$

where I is the detected signal (dark field projection value) at the detector pixel, $I_0$ is the unattenuated detected signal, l is the position along the x-ray from the source 102 (l=0) through the object 114 to a detector pixel of the detector array 104 (l=1), f(·) is the the distribution of the object property, $\vec{S}$ is the source position, and $\vec{r}$ is a unit vector along the x-ray from the source 102 to the phase grating 112. Logging both sides of the equations renders a linear equation representing the line integral of the attenuation coefficient along a path, as shown in EQUATION 2:

$$h = -\ln\left(\frac{I}{I_0}\right) = \int_0^1 If(\vec{S} + \vec{tr})dl, \qquad \text{EQUATION 2}$$

where h is the measurable signal. The goal is to reconstruct the distribution of the property f(·) along the ray $\vec{r}$.

Unfortunately, to rotate the source 102, the gratings 108, 110 and 112, and the detector array 104, the imaging system must at least include a rotating frame that supports the source 102, the detector and the gratings 108, 110 and 112, a stationary frame and bearing to support the rotating frame, a belt, chain, magnetic or other drive system along with a motor and controller to rotate the rotating frame, and one or more encoders or the like to determine angular position information, which adds complexity and cost to the overall dark field imaging system. In addition, the rotating components are under g forces, which cause dynamic structural changes to the rotating components during each rotation, which may increase the mechanical requirements and tolerances of the phase stepping components so the grating is accurately stepped for each measurement.

Aspects described herein address the above-referenced problems and others.

In one aspect, a method for dark-field imaging includes acquiring dark-field image projections of an object with an imaging apparatus that includes an x-ray interferometer, applying a pressure wave having a predetermined frequency to the object for each acquired projection, wherein the predetermined frequency is different for each projection, and processing the acquired projections, thereby generating a 3D image of the object.

In another aspect, an imaging system includes a scanner configured for dark-field imaging, the scanner including: a source/detector pair and a subject support, a pressure wave generator configured to generate and transmit pressure waves having predetermined frequencies, and a console that controls the scanner and the pressure wave generator to acquire at least two dark-field projection of an object with different pressure waves having different frequencies applied to the object.

In another aspect, a method includes generating a 3D dark-field image of an object with data acquired without a relative movement between a source/detector pair of an imaging system scanning the object and the object and by applying pressure waves having different frequencies for each acquired projection.

The invention may take form in various components and arrangements of components, and in various steps and arrangements of steps. The drawings are only for purposes of illustrating the preferred embodiments and are not to be construed as limiting the invention.

FIG. 1 schematically illustrates a prior art apparatus configured for dark-field imaging.

FIGS. 2 and 3 schematically illustrate how object position magnification along a ray affects dark-field imaging.

Figure 4:
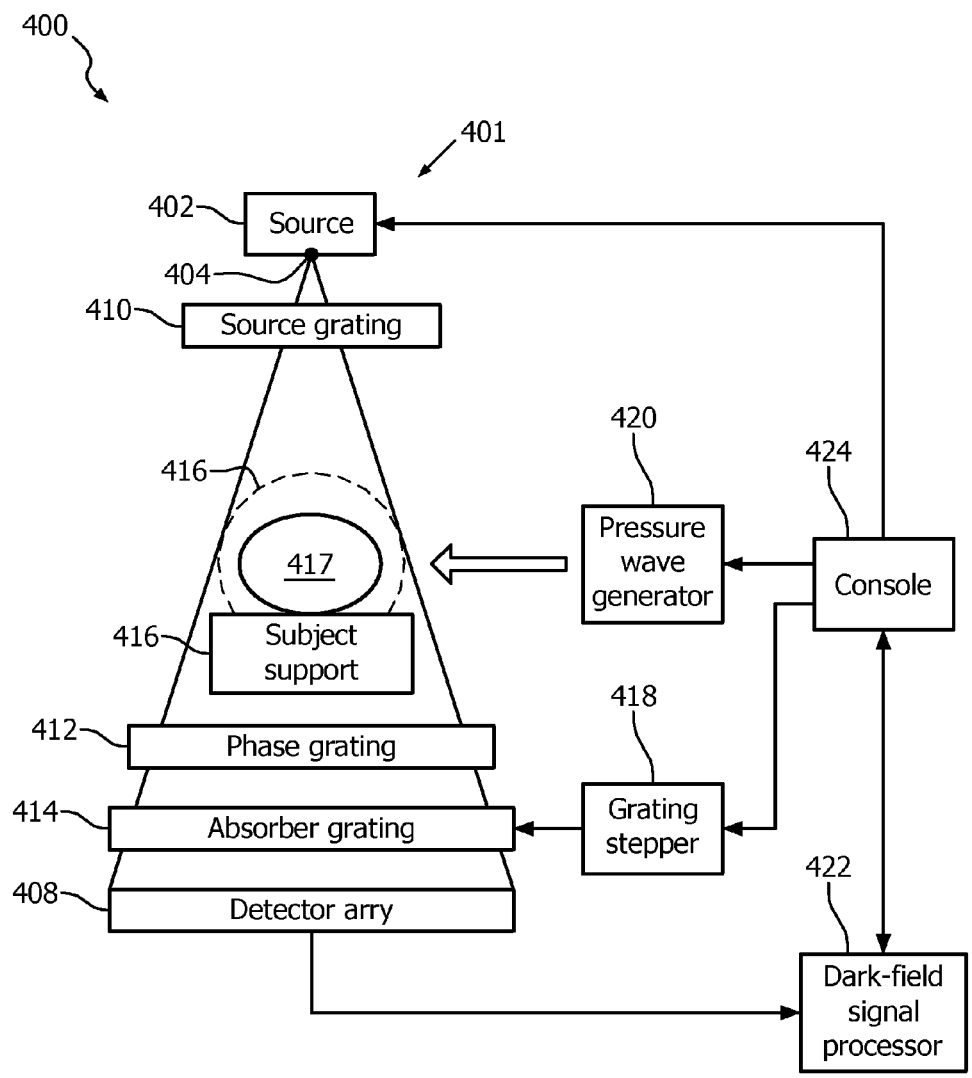

FIG. 4 schematically illustrates an imaging system configured for 3D dark-field grating-based DPCI imaging.

Figure 5:
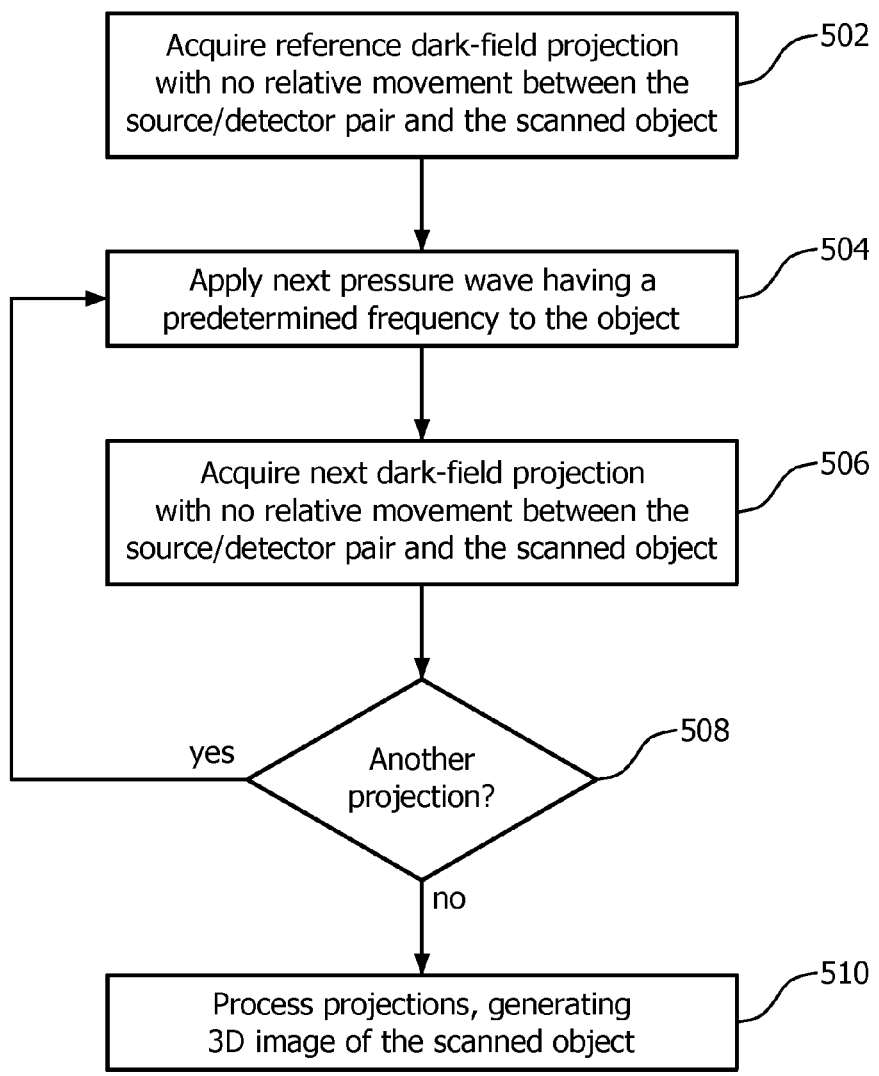

FIG. 5 illustrates an example method for 3D dark-field grating-based DPCI imaging.

Referring to FIG. 4, an imaging system 400 includes a scanner 401 configured for at least 3D dark-field imaging is schematically illustrated. The scanner 401 includes a radiation source 402 (e.g., an X-ray tube) with a focal spot 404 that emits radiation that traverse an examination region 406 and an object 417 or subject therein. A radiation sensitive detector array 408 is located opposite the radiation source 402 across the examination region 406. The radiation sensitive detector array 408 detects radiation traversing the examination region 406 and generates a signal indicative thereof, including a dark-field signal in connection with dark-field imaging.

An X-ray imaging interferometer includes three grating structures, a source grating 410, a phase grating 412 and an absorber grating 414. The source grating 410, phase grating 412 and absorber grating 414 respectively have grating line periods and are separated by distances, e.g., as discussed in application Ser. No. 13/514,682, filed Jun. 8, 2012, entitled "Phase Contrast Imaging," and assigned to Koninklijke Philips Electronics N.V., the entirety of which is incorporated herein by reference. Generally, the source grating 410 is adjacent to the focal spot 404 in the path of the radiation, acts as an absorbing mask with transmitting slits, filters the emitted radiation beam, and creates individual coherent (but mutually incoherent) sources.

The object causes refraction of coherent x-rays that is proportional to the local gradient of the real part of the refractive index of the object, and the angular deviation results in changes of the locally transmitted intensity through the phase grating 412. The phase grating 412 is located adjacent to the object and acts as a beam splitter, dividing an incoming x-ray into diffracted beams that interfere and form linear periodic fringe patterns. The absorber grating 414 acts as a transmission mask for the detector 408 and transforms local fringe positions into signal intensity variations. The phase/absorber gratings 412/414 can be considered a multi-collimator translating the angular deviations into changes of the locally transmitted intensity, which can be detected with a standard or other imaging detector array.

The phase grating 412 and the absorber grating 414 are configured to translate, relative to one another, in a transverse direction, perpendicular to the z-axis. This includes translating one or both (in a same direction with different speeds or an opposing direction with the same or different speed) of the phase grating 412 and the absorber grating 414 in the transverse direction. For explanatory purposes, the following will be discussed with respect to a configuration in which the absorber grating 414 translates. A grating stepper 418 controls translation (i.e., stepping) of the absorber grating 414 at least based on a phase stepping algorithm which moves the absorber grating 414 in predetermined discrete step size increments.

A pressure wave generator 420 generates and transmits a pressure wave that traverses the examination region 406 and the object 417 therein. The pressure wave generator 420 may include a transducer or the like that can convert one form of energy (e.g., electrical) into a pressure wave of a predetermined frequency. Suitable frequencies are frequencies between one Hertz (1 Hz) and one thousand Hertz (1000 Hz), which cause compression and/or vibration of the material of the object 417 that results in physical deformation of the object 417 in the examination region 406 which is similar to actual physical displacement of the object 417 in the examination region 406.

A general-purpose computing system or computer serves as an operator console 424. The console 424 includes a human readable output device such as a monitor and an input device such as a keyboard, mouse, etc. Software resident on the console 424 allows the operator to interact with and/or operate the imaging system 400. Such interaction includes selecting a dark-field imaging scan protocol which utilizes the pressure wave generator 420, initiate scanning, etc. A subject support 416 supports the object 417 in the examination region 406.

With one dark-field imaging protocol, the pressure wave generator 420 is invoked to transmit a pressure wave that traverses the object 417 and the grating stepper 418 steps the absorber grating 414 through phase coding steps for acquisition of a projection, a pressure wave having a different frequency is generated for different projections, and the projections are acquired with no relative movement between the source/detector pair 402/408 and the object 417. The number of phase coding steps and/or projections can be default, user defined, and/or otherwise determined.

With such an algorithm, the pressure waves interacts with the material of the object 417 and such interactions result in different material deformations of the object 417 for each projection, which, effectively, is similar to physically moving the object 417 along a ray path between the source 402 and the detector array 408. Since the dark field signal h is a function of distance of the object 417 from the source 402, the resulting set of projections include information that can be used to determine attenuation along each ray, which is described is greater detail next.

As discussed above, the dark field signal h has been represented as shown in EQUATION 2, which is reproduced below:

$$h = -\ln\left(\frac{I}{I_0}\right) = \int_0^1 lf(\vec{S} + l\vec{r})dl. \qquad \text{EQUATION 2}$$

Because of the low compressibility of tissue, tissue reacts with a local displacement in a pressure wave. Under ideal conditions, the displacement $\Delta_l$ can be model along $\vec{r}$ under a pressure wave excitation as shown in EQUATION 3:

$$\Delta_l a e^{-i(tk_t + (\vec{S} + l\vec{r})k\vec{r})}, \qquad \text{EQUATION 3}$$

where a is the amplitude of the displacement, i is sqrt(−1), $k_t$ is the frequency of the sound wave, $k_r$ is the wavelength, and t is time. For a snapshot (t=constant), a constant part C (for each ray) can be separated from the displacement along $\vec{r}$ using a parameter l as shown in EQUATION 4:

$$\Delta_{M,l} = C_M e^{-ilk_M l}, \qquad \text{EQUATION 4}$$

where M is a set of wave excitation parameters and M={$a_M$, $C_M$, $k_{J,l}$}.

The dark field imaging measurement h, as a function of local displacement, and based on EQUATIONS 2 and 4, can be expressed as shown in in EQUATION 5:

$$h(M) = \int (l + \Delta_{M,l}) f(\vec{S} + l\vec{r}) dl. \qquad \text{EQUATION 5}$$

With a reference measurement $h(M_O)$, $\Delta_{M_0,l}=0$, EQUATION 5 can be written as shown in EQUATION 6:

$$h(M)=h(M_0)\int \Delta_{M,l}f(\vec{S}+l\vec{r})dl=h(M_0)+C_M\int e^{-ilk_M l}f(\vec{S}+l\vec{r})dl. \qquad \text{EQUATION 6}$$

With a set of modulations, EQUATION 6 becomes a Fourier transformation.

A dark-field signal processor 422 processes the dark-field signals generated and output by the detector array 408, producing 3D data of the scanned object 417. This includes inverting the Fourier transformation and reconstructing the distribution of the property f(·) along the ray $\vec{r}$, creating a 3D image of the object. Where inhomogeneous elastic properties of the tissue disturb the displacement field, an iterative reconstruction and a discrete formulation of the measurement can be used to solve for an elasticity field and the dark field in one combined reconstruction.

FIG. 5 illustrates an example dark field imaging method with no physical movement of the source/detector pair 402/480 and the object 417 between projections.

It is to be appreciated that the ordering of the acts is not limiting. As such, other orderings are contemplated herein. In addition, one or more acts may be omitted and/or one or more additional acts may be included.

At 502, a reference projection of a dark-field scan of the object 417 is acquired with no relative movement between the source/detector pair 402/480 and the object 417.

At 504, a pressure wave having a predetermined frequency is applied to the object, which causes a deformation of the object 417 similar to actual physical displacement of the object 417 along a ray path between the source 402 and the detector 408.

At 506, a next projection of the dark-field scan of the object 417 under the first deformation is acquired with no relative movement between the source/detector pair 402/480 and the object 417.

At 508 it is determined whether another projection is to be acquired.

If so, then acts 504 and 506 are repeated with a pressure wave having a next different frequency.

If not, then at 510 the projections are processed to generate a 3D image of the object 417.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for x-ray dark-field imaging, comprising:
   acquiring x-ray dark-field image projections of an object with an imaging apparatus that includes an x-ray interferometer;
   applying a pressure wave having a predetermined frequency to the object for each acquired projection, wherein the predetermined frequency is different for each projection; and
   processing the acquired projections, thereby generating a 3D image of the object.

2. The method of claim 1, wherein the pressure wave causes a deformation of material of the object.

3. The method of claim 1, wherein the projection is acquired with no relative movement between a source/detector pair of the imaging apparatus and a subject support of the imaging apparatus supporting the object for the scan.

4. The method of claim 1, wherein a pressure is applied to the object during acquisition of a projection.

5. The method of claim 1, further comprising:
   acquiring a reference x-ray dark-field image projection without any pressure wave applied to the object.

6. The method of claim 1, wherein the predetermined frequency is a frequency in a range of 1 Hz. to 1000 Hz.

7. The method of claim 1, wherein the acquired projections represent a Fourier transformation.

8. The method of claim 7, further comprising:
generating the 3D image of the object by inverting the Fourier transform and reconstructing a distribution along each ray traversing the object.

9. The method of claim 1, further comprising:
iteratively reconstructing and a discrete formulation of the acquired projections, thereby solving an elasticity field and the x-ray dark-field in a single combined reconstruction.

10. The method of claim 1, further comprising:
stepping an absorber grating of an interferometer of the imaging apparatus to phase code the projection.

11. An imaging system, comprising:
a scanner configured for x-ray dark-field imaging, the scanner including: an x-ray interferometer, a source/detector pair and a subject support;
a pressure wave generator configured to generate and transmit pressure waves having predetermined frequencies; and
a console that controls the scanner and the pressure wave generator to acquire at least two x-ray dark-field projections of an object with different pressure waves having different frequencies applied to the object.

12. The imaging system of claim 11, wherein the pressure wave causes a deformation of material of the object.

13. The imaging system of claim 11, wherein the interferometer, includes:
a source grating,
a phase grating, and
an absorber grating; and
a grating stepper that steps at least one of the phase grating or the absorber grating with respect to the other to phase code the projections.

14. The imaging system of claim 11, wherein the projection is acquired with no relative movement between the source/detector pair and the subject support.

15. The imaging system of claim 11, wherein the console controls the scanner and the pressure wave generator to acquire a reference x-ray dark-field projection of the object with no pressure applied to the object.

16. The imaging system of claim 11, wherein the predetermined frequency is a frequency in a range of 1 Hz. to 1000 Hz.

17. The imaging system of claim 11, further comprising:
a x-ray dark-field signal processor that processes acquired x-ray dark-field signals and generates a 3D image of the object.

18. The imaging system of claim 17, wherein the acquired x-ray dark-field signals represent a Fourier transformation, and the x-ray dark-field signal processor inverts the Fourier transform and reconstructs a distribution along each ray traversing the object, thereby generating the 3D image of the object.

19. The imaging system of claim 11, further comprising:
a x-ray dark-field signal processor that iteratively reconstructs and a discrete formulation of the acquired projections, thereby solving an elasticity field and the dark field in a single combined reconstruction.

20. A non-transitory computer readable medium encoded with computer readable instructions, which, when executed by a processor, causes the processor to:
control an imaging system to acquire x-ray dark-field image projections of an object with an x-ray interferometer and a source/detector pair;
control a pressure wave generator to apply a pressure wave having a predetermined frequency to the object for each acquired projection, wherein the predetermined frequency is different for each projection; and
control the imaging system and the pressure wave generator to acquire at least two x-ray dark-field projections of an object with different pressure waves having different frequencies applied to the object.

21. The non-transitory computer readable medium of claim 20, wherein the computer readable instructions further cause the processor to:
control a signal processor to generate a 3D image of the object with the acquired projections.

22. The non-transitory computer readable medium of claim 20, wherein the computer readable instructions further cause the processor to:
control a grating stepper that steps at least one of a phase grating or an absorber grating of the interferometer with respect to the other of the at least one of a phase grating or an absorber grating to phase code the projections.

* * * * *